United States Patent
Kawamura

(10) Patent No.: US 10,136,873 B2
(45) Date of Patent: Nov. 27, 2018

(54) RADIOGRAPHIC IMAGE PROCESSING DEVICE, METHOD, AND RECORDING MEDIUM

(71) Applicant: FUJIFILM Corporation, Tokyo (JP)

(72) Inventor: Takahiro Kawamura, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 85 days.

(21) Appl. No.: 15/265,030

(22) Filed: Sep. 14, 2016

(65) Prior Publication Data

US 2017/0055933 A1 Mar. 2, 2017

Related U.S. Application Data

(63) Continuation of application No. PCT/JP2015/001211, filed on Mar. 6, 2015.

(30) Foreign Application Priority Data

Mar. 24, 2014 (JP) ................................. 2014-059841

(51) Int. Cl.
*G06K 9/00* (2006.01)
*A61B 6/00* (2006.01)
(Continued)

(52) U.S. Cl.
CPC ............ *A61B 6/5282* (2013.01); *A61B 6/461* (2013.01); *A61B 6/5211* (2013.01);
(Continued)

(58) Field of Classification Search
None
See application file for complete search history.

(56) References Cited

U.S. PATENT DOCUMENTS 5,278,754 A 1/1994 Arakawa
5,615,279 A * 3/1997 Yoshioka .............. G06T 11/005
378/7

(Continued)

FOREIGN PATENT DOCUMENTS

JP 62-192640 A 8/1987
JP 2-244881 A 9/1990
(Continued)

OTHER PUBLICATIONS

Fivez, C., Vuylsteke, P., Wambacq, P., Suetens, P., & Schoeters, E. (Sep. 1996). Multi-resolution contrast amplification in digital radiography with compensation for scattered radiation. In Image Processing, 1996. Proceedings., International Conference on (vol. 1, pp. 339-342). IEEE.*

(Continued)

*Primary Examiner* — Vu Le
*Assistant Examiner* — Samah A Beg
(74) *Attorney, Agent, or Firm* — Sughrue Mion, PLLC

(57) ABSTRACT

A frequency decomposition unit performs frequency decomposition for a first radiographic image to acquire a plurality of band images. A scattered radiation removal unit calculates a scattered radiation component that is caused by a subject and is included in a second radiographic image which has a linear relationship with the amount of radiation, using the second radiographic image, and removes the scattered radiation component from the second radiographic image to acquire a scattered-radiation-removed radiographic image. A conversion function determination unit determines a conversion function for converting at least one of the band images according to the scattered radiation component included in the second radiographic image. A reconstruction unit converts the band image, using the conversion function, and generates a converted band image. The reconstruction
(Continued)

unit reconstructs the scattered-radiation-removed radiographic image and the converted band image to acquire a processed radiographic image.

10 Claims, 12 Drawing Sheets

(51) Int. Cl.
   *G06T 11/00* (2006.01)
   *G06T 7/00* (2017.01)

(52) U.S. Cl.
   CPC .......... *A61B 6/5235* (2013.01); *G06T 7/0012* (2013.01); *G06T 11/005* (2013.01); *G06T 2207/10124* (2013.01)

(56) References Cited

U.S. PATENT DOCUMENTS

| | | | |
|---|---|---|---|
| 6,385,287 B1* | 5/2002 | Dorner | A61B 6/00 378/154 |
| 7,283,605 B2* | 10/2007 | Sainath | G06T 11/005 378/207 |
| 7,474,774 B2* | 1/2009 | Inoue | G06T 5/002 348/E5.086 |
| 8,064,676 B2 | 11/2011 | Li et al. | |
| 8,155,412 B2 | 4/2012 | Kitamura | |
| 9,307,949 B2* | 4/2016 | Tsubota | A61B 6/032 |
| 9,538,975 B2* | 1/2017 | Silver | A61B 6/5282 |
| 9,704,241 B2* | 7/2017 | Imai | G06T 7/0012 |
| 9,836,830 B2* | 12/2017 | Naito | G06T 5/008 |
| 2005/0243963 A1* | 11/2005 | Ghelmansarai | A61B 6/00 378/7 |
| 2007/0104310 A1* | 5/2007 | Nottling | A61B 6/5282 378/4 |
| 2008/0075347 A1* | 3/2008 | Ruhrnschopf | G06T 11/005 382/131 |
| 2009/0290682 A1* | 11/2009 | Star-Lack | G06T 11/005 378/87 |
| 2012/0008849 A1 | 1/2012 | Reboni et al. | |
| 2012/0177278 A1 | 7/2012 | Kitamura | |
| 2013/0108137 A1 | 5/2013 | Kitamura | |
| 2014/0023252 A1 | 1/2014 | Imai | |
| 2014/0334700 A1* | 11/2014 | Yang | G06T 11/005 382/130 |
| 2014/0363071 A1* | 12/2014 | Imai | A61B 6/4291 382/132 |
| 2015/0251018 A1* | 9/2015 | Tajima | A61B 6/4233 378/28 |
| 2015/0317771 A1* | 11/2015 | Kato | A61B 6/5205 382/132 |
| 2015/0379711 A1* | 12/2015 | Imai | A61B 6/5282 382/132 |
| 2016/0235384 A1* | 8/2016 | Enomoto | A61B 6/4291 |
| 2016/0235385 A1* | 8/2016 | Enomoto | A61B 6/463 |
| 2016/0249875 A1* | 9/2016 | Enomoto | A61B 6/5282 378/62 |
| 2016/0267630 A1* | 9/2016 | Naito | G01N 23/046 |
| 2016/0296192 A1* | 10/2016 | Noda | A61B 6/5282 |
| 2016/0354050 A1* | 12/2016 | Enomoto | A61B 6/4283 |
| 2016/0354051 A1* | 12/2016 | Enomoto | A61B 6/4241 |
| 2017/0221207 A1* | 8/2017 | Imai | G06T 7/0012 |
| 2017/0231593 A1* | 8/2017 | Fukuda | A61B 6/032 382/132 |
| 2017/0273649 A1* | 9/2017 | Tajima | A61B 6/50 |
| 2017/0296133 A1* | 10/2017 | Katsumata | A61B 6/5282 |
| 2017/0360391 A1* | 12/2017 | Kawamura | A61B 6/5282 |
| 2017/0364635 A1* | 12/2017 | Kobayashi | G06F 19/321 |
| 2018/0106734 A1* | 4/2018 | Lang | A61B 6/5282 |

FOREIGN PATENT DOCUMENTS

| | | |
|---|---|---|
| JP | 4-180056 A | 6/1992 |
| JP | 7-124150 A | 5/1995 |
| JP | 8-266529 A | 10/1996 |
| JP | 9-24039 A | 1/1997 |
| JP | 2002-171444 A | 6/2002 |
| JP | 2003-260053 A | 9/2003 |
| JP | 2009-61253 A | 3/2009 |
| JP | 2012-518858 A | 8/2012 |
| JP | 2012-203504 A | 10/2012 |
| JP | 2013-240696 A | 12/2013 |

OTHER PUBLICATIONS

Christiaan Fivez et al., "Multi-Resolution Contrast Amplification in Digital Radiography with Compensation for Scattered Radiation", IEEE, 1996, pp. 339-342, vol. 1.

Dinko E. Gonzalez Trotter et al., "Thickness-dependent Scatter Correction Algorithm for Digital Mammography", Proc. SPIE, 2002, pp. 469-478, vol. 4682.

John M. Boone et al., "An analytical model of the scattered radiation distribution in diagnostic radiology", Med. Phys., Sep./Oct. 1988, pp. 721-725, vol. 15, No. 5.

International Search Report for PCT/JP2015/001211 dated Jun. 23, 2015.

Written Opinion for PCT/JP2015/001211 dated Jun. 23, 2015.

* cited by examiner

RADIOGRAPHIC IMAGE PROCESSING DEVICE, METHOD, AND RECORDING MEDIUM

CROSS REFERENCE TO RELATED APPLICATIONS

The present application is a Continuation of PCT International Application No. PCT/JP2015/001211 filed on Mar. 6, 2015, which claims priority under 35 U.S.C. § 119(a) to Japanese Patent Application No. 2014-059841 filed on Mar. 24, 2014. Each of the above applications is hereby expressly incorporated by reference, in its entirety, into the present application.

BACKGROUND OF THE INVENTION

1. Field of the Invention

The present invention relates to a radiographic image processing device and a radiographic image processing method which perform image processing including a scattered radiation removal process for a radiographic image and a program which causes a computer to perform the radiographic image processing method.

2. Description of the Related Art

In the related art, in the capture of a radiographic image of a subject using radiation that is transmitted through the subject, particularly, when the thickness of the subject is large, the radiation is scattered in the subject and the scattered radiation (hereinafter, also referred to a scattered ray) causes a reduction in the contrast of the acquired radiographic image. For this reason, in some cases, when a radiographic image is captured, a scattered radiation removal grid (hereinafter, simply referred to as a grid) is provided between a subject and a radiation detector which detects radiation and acquires a radiographic image such that the scattered radiation is not emitted to the radiation detector. When imaging is performed using the grid, radiation which is scattered by the subject is less likely to be emitted to the radiation detector. Therefore, it is possible to improve the contrast of the radiographic image.

In contrast, when imaging is performed using the grid, a subject image and a fine stripe pattern (moire) corresponding to the grid are included in the radiographic image, which makes it difficult to see the image.

Therefore, a method has been proposed which captures a radiographic image, without using a grid, and gives an image quality improvement effect, which can be obtained by removing scattered radiation, to the acquired radiographic image through image processing on the basis of imaging conditions (see U.S. Pat. No. 8,064,676B, JP2013-240696A, and C. Fivez et al., "Multi-resolution contrast amplification in digital radiography with compensation for scattered radiation", 1996 IEEE, pp. 339-342). The methods described in U.S. Pat. No. 8,064,676B and C. Fivez et al., "Multi-resolution contrast amplification in digital radiography with compensation for scattered radiation", 1996 IEEE, pp. 339-342 decompose a radiographic image into a plurality of frequency components, perform a process of controlling contrast for a low-frequency component which is regarded as a scattered radiation component, perform a contrast enhancement process for a high-frequency component in order to prevent a reduction in contrast due to the removal of the scattered radiation component, and combine the processed frequency components to acquire a radiographic image from which the scattered radiation component has been removed.

In the method described in U.S. Pat. No. 8,064,676B, the scattered radiation removal process is performed by multiplying a low-frequency component by a gain corresponding to the pixel value of the low-frequency component. Here, the gain is less than 1. The gain has a smaller value in a lower frequency band and is reduced as the pixel value increases. In contrast, a high-frequency component is multiplied by a gain of more than 1 to enhance the contrast of the radiographic image, in order to compensate for a reduction in contrast. In addition, the gain of a high-frequency component with high contrast is non-linearly controlled in order to prevent the over-enhancement of a high-contrast object (for example, a bone or metal) included in a radiographic image.

According to the methods disclosed in U.S. Pat. No. 8,064,676B, JP2013-240696A, and C. Fivez et al., "Multi-resolution contrast amplification in digital radiography with compensation for scattered radiation", 1996 IEEE, pp. 339-342, since no grid is required during imaging, it is possible to reduce a burden on a patient during imaging. In addition, it is possible to remove scattered radiation and to obtain a radiographic image with improved contrast while preventing the deterioration of image quality due to density unevenness and moire.

It is known that, when a radiographic image of a subject is captured using radiation that is transmitted through the subject, the amount of radiation scattered in the subject increases and the influence on a reduction in radiation transmittance increases as the thickness of the subject increases, which results in a variation in the quality of the acquired radiographic image. For this reason, a technique has been proposed which roughly estimates the thickness of a subject, on the basis of various kinds of information, such as imaging conditions, a signal value of a radiographic image, the width of the histogram of the signal value of the radiographic image, and the length of the subject in a predetermined direction in the radiographic image, and changes the conditions of imaging processing, such as a scattered radiation removal process for the captured radiographic image, or imaging conditions applied to capture a radiographic image, on the basis of the estimated thickness of the subject.

For example, JP1990-244881A (JP-H02-244881A) discloses a method that measures pixel values of a radiograph image of a simulated subject with a known thickness which is captured under known imaging conditions, prepares a correspondence table in which a body thickness is associated with the pixel value in advance, roughly estimates a body thickness distribution on the basis of the pixel value of the radiographic image with reference to the correspondence table, estimates a scattered radiation component of the radiographic image corresponding to the body thickness distribution of the radiographic image, and subtracts the scattered radiation component from the radiographic image to acquire a processed image.

In addition, Trotter et al., "Thickness-dependent Scatter Correction Algorithm for Digital Mammography", Proc. SPIE, Vol. 4682, May 2002, pp. 469-478 discloses a method which estimates a scattered radiation component of a radiographic image on the basis of a human body thickness distribution and removes the scattered radiation component. The method disclosed in Trotter et al., "Thickness-dependent Scatter Correction Algorithm for Digital Mammography", Proc. SPIE, Vol. 4682, May 2002, pp. 469-478 applies a predetermined function to an input radiographic image on the basis of the body thickness distribution estimated from the pixel value of the radiographic image to generate an estimated scattered radiation image, which is obtained by estimating an image of scattered radiation included in the radiographic image, and subtracts the estimated scattered radiation image from the radiographic image to generate an estimated primary radiation image which is obtained by estimating a primary radiation image from the input radiographic image. In addition, the method repeatedly performs a process which applies a predetermined function to the generated estimated primary radiation image to generate an estimated scattered radiation image and subtracts the estimated scattered radiation image from the radiographic image to generate an estimated primary radiation image until the estimated scattered radiation image converges under predetermined convergence conditions, calculates a converged estimated scattered radiation image, and subtracts the estimated scattered radiation image from the radiographic image to finally obtain a processed image from which the scattered component has been removed. In addition, C. Fivez et al., "Multi-resolution contrast amplification in digital radiography with compensation for scattered radiation", 1996, IEEE, pp. 339-342 discloses a method which adjusts a predetermined function for estimating an image of scattered radiation included in the radiographic image according to the body thickness.

However, in the radiographic image, the attenuation of radiation which varies depending on the internal composition (a material and the density of the material) of the subject is represented by the shade of an image and the pixel value of the radiographic image corresponds to the amount of radiation transmitted through the subject. Here, when the amount of radiation which is incident on the subject is Iin, a linear attenuation coefficient corresponding to the composition of radiation is $\mu$, and a thickness is t, a value Iout of each pixel of a radiographic image is represented by Iout=Iin·$e^{-\mu t}$. A radiation detector performs logarithmic conversion for a signal acquired at each pixel position. Therefore, the value of each pixel of the radiographic image has a linear relationship with the logarithmic amount of radiation. That is, the value of each pixel can be represented by log(Iout)=log(Iin)+(-$\mu$t). Then, the radiographic image which has been subjected to the logarithmic conversion so as to have a linear relationship with the logarithmic amount of radiation is converted into a digital signal and image processing for improving image quality, such as a gradation process, frequency processing, and a dynamic range compression process, is performed to acquire a high-quality radiographic image.

Since the value of each pixel of the acquired radiographic image has a linear relationship with the amount of radiation subjected to logarithmic conversion, a difference in the thickness and composition of the subject can be reflected in the captured image of the subject without any change. Therefore, it is possible change the pixel value using a linear operation for the pixel value and thus to reproduce image processing, such as a gradation process, frequency processing, and a dynamic range compression process, with the same degree of enhancement, regardless of a radiographic image. For example, in the methods disclosed in U.S. Pat. No. 8,064,676B and C. Fivez et al., "Multi-resolution contrast amplification in digital radiography with compensation for scattered radiation", 1996, IEEE, pp. 339-342, a low-frequency component is multiplied by a gain of less than 1 to suppress a scattered radiation component and a high-frequency component is multiplied by a gain of more than 1 to enhance contrast. This method can be used since the radiographic image has a linear relationship with the logarithmic amount of radiation. Therefore, when image processing is performed for the radiographic image which has a linear relationship with the amount of radiation subjected to logarithmic conversion, it is possible to acquire a high-quality radiographic image suitable for diagnosis, regardless of imaging conditions.

SUMMARY OF THE INVENTION

When radiation passes through a material in the subject, the direction of a portion of the radiation is changed and scattered radiation is generated. It is necessary to calculate the sum of scattered radiation components from the values of neighboring pixels in order to estimate the scattered radiation component at a certain pixel position of the radiographic image using, for example, the methods disclosed in JP1990-244881A (JP-H02-244881A) and Trotter et al., "Thickness-dependent Scatter Correction Algorithm for Digital Mammography", Proc. SPIE, Vol. 4682, May 2002, pp. 469-478. Here, since the scattered radiation component corresponds to the amount of radiation, it is necessary to use a radiographic image in which a pixel value has a linear relationship with the amount of radiation, in order to calculate the scattered radiation component.

Therefore, a method may be considered which calculates a scattered radiation component using a radiographic image that has a linear relationship with the amount of radiation and performs a scattered radiation removal process and a contrast enhancement process. In this case, the scattered radiation component is subtracted from a low-frequency component of the radiographic image and the gain is added to a high-frequency component. In this way, it is possible to enhance contrast while removing scattered radiation.

However, in the radiographic image that has a linear relationship with the amount of radiation, it is difficult to change the pixel value using a linear operation. Therefore, it is difficult to uniquely determine the gain. In particular, it is difficult to determine a non-linear gain for preventing over-enhancement in the radiographic image that has a linear relationship with the amount of radiation. For this reason, when the radiographic image that has a linear relationship with the amount of radiation is used, it is difficult to accurately enhance contrast. Conversely, a method may be considered which calculates a scattered radiation component using a radiographic image that has a linear relationship with the logarithmic amount of radiation. In this case, as described above, since the scattered radiation is a portion of radiation, it is difficult to calculate the scattered radiation component using the radiographic image that has a linear relationship with the logarithmic amount of radiation.

The invention has been made in view of the above-mentioned problems and an object of the invention is to provide a technique which can effectively prevent a reduction in contrast caused by scattered radiation of a radiographic image with high accuracy.

A radiographic image processing device according to the invention comprises: frequency decomposition means for performing frequency decomposition for a first radiographic image which is captured by irradiating a subject with radiation and acquiring a plurality of band images indicating a plurality of frequency components of the first radiographic image; scattered radiation removal means for calculating a scattered radiation component that is caused by the subject and is included in a second radiographic image of the subject which has a linear relationship with an amount of radiation, using the second radiographic image, and removing the scattered radiation component from the second radiographic image to acquire a scattered-radiation-removed radiographic image; conversion function determination means for determining a conversion function for converting at least one of the band images according to the scattered radiation component included in the second radiographic image; conversion means for converting the at least one band image, using the conversion function, and generating a converted band image; and reconstruction means for reconstructing the scattered-radiation-removed radiographic image and the converted band image to acquire a processed radiographic image.

In the radiographic image processing device according to the invention, the conversion function determination means may determine the conversion function on the basis of a ratio of the scattered radiation component to a sum of a primary radiation component included in the radiation and the scattered radiation component.

In the radiographic image processing device according to the invention, the scattered radiation removal means may calculate the scattered radiation component and the primary radiation component, using a body thickness distribution of the subject. The conversion function determination means may calculate the ratio from the calculated scattered radiation component and the calculated primary radiation component.

The radiographic image processing device according to the invention may further comprise body thickness estimation means for estimating the body thickness distribution on the basis of the second radiographic image.

In the radiographic image processing device according to the invention, the first radiographic image may have a pixel value that has a linear relationship with a logarithmic amount of radiation.

In the radiographic image processing device according to the invention, the second radiographic image may be obtained by performing inverse logarithmic conversion for the first radiographic image.

In the radiographic image processing device according to the invention, the reconstruction means may perform logarithmic conversion for the scattered-radiation-removed radiographic image and reconstruct the logarithmically-converted scattered-radiation-removed radiographic image and the converted band image to acquire the processed radiographic image.

The radiographic image processing device according to the invention may further comprise characteristic acquisition means for acquiring virtual grid characteristics which are characteristics of a virtual grid that is assumed to be used in order to remove scattered radiation when an image of the subject is captured. The scattered radiation removal means may calculate the scattered radiation component on the basis of the virtual grid characteristics. The conversion function determination means may determine the conversion function on the basis of the calculated scattered radiation component.

In the radiographic image processing device according to the invention, when a pixel value of the band image is greater than a predetermined threshold value, the conversion function determination means may determine the conversion function such that the pixel value is suppressed.

A radiographic image processing method according to the invention comprises: performing frequency decomposition for a first radiographic image which is captured by irradiating a subject with radiation and acquiring a plurality of band images indicating a plurality of frequency components of the first radiographic image; calculating a scattered radiation component that is caused by the subject and is included in a second radiographic image of the subject which has a linear relationship with an amount of radiation, using the second radiographic image; removing the scattered radiation component from the second radiographic image to acquire a scattered-radiation-removed radiographic image; determining a conversion function for converting at least one of the band images according to the scattered radiation component included in the second radiographic image; converting the at least one band image, using the conversion function, and generating a converted band image; and reconstructing the scattered-radiation-removed radiographic image and the converted band image to acquire a processed radiographic image.

A program that causes a computer to perform the radiographic image processing method according to the invention may be provided.

According to the invention, frequency decomposition is performed for the first radiographic image to acquire a plurality of band images indicating a plurality of frequency components of the first radiographic image. In addition, the scattered radiation component that is caused by the subject and is included in the second radiographic image which has a linear relationship with the amount of radiation is calculated, using the second radiographic image, and the scattered radiation component is removed from the second radiographic image to acquire the scattered-radiation-removed radiographic image. Then, the conversion function for converting at least one of the band images is determined according to the scattered radiation component included in the second radiographic image. The at least one band image is converted by the conversion function to generate the converted band image. The scattered-radiation-removed radiographic image and the converted band image are reconstructed to acquire the processed radiographic image.

Here, since the second radiographic image has a linear relationship with the amount of radiation, it is possible to accurately calculate the scattered radiation component. As a result, it is possible to accurately remove the scattered radiation component from the second radiographic image. Since the conversion function is calculated from the scattered radiation component of the second radiographic image which has a linear relationship with the amount of radiation, it is possible to accurately enhance the band image using the conversion function. Therefore, in the reconstructed radiographic image, scattered radiation is removed and a high-frequency component included in the radiographic image is enhanced. As a result, a reduction in contrast caused by scattered radiation is prevented.

In particular, the first radiographic image has a linear relationship with the logarithmic amount of radiation and the pixel value of the band image has a linear relationship with the logarithmic amount of radiation. Therefore, it is possible to easily determine the conversion function from the scattered radiation component. In addition, since the band image is converted by the conversion function, it is possible to effectively enhance a frequency component of the band image. Therefore, it is possible to accurately and effectively prevent a reduction in contrast caused by scattered radiation of a radiographic image.

DESCRIPTION OF THE PREFERRED EMBODIMENTS

Figure 1:
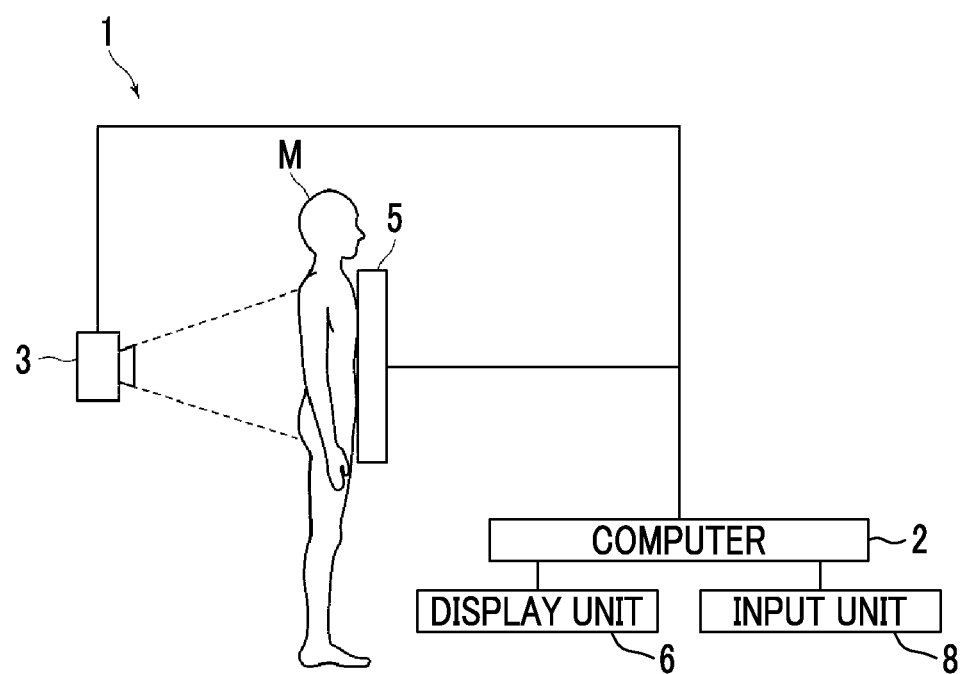
FIG. 1 is a block diagram schematically illustrating the structure of a radiography system to which a radiographic image processing device according to a first embodiment of the invention is applied.

Hereinafter, embodiments of the invention will be described with reference to the drawings. FIG. 1 is a block diagram schematically illustrating the structure of a radiography system to which a radiographic image processing device according to a first embodiment of the invention is applied. As illustrated in FIG. 1, the radiography system according to the first embodiment performs various types of image processing including a scattered radiation removal process for a radiographic image of a subject, and comprises an imaging device 1 and a computer 2 including the radiographic image processing device according to this embodiment, as illustrated in FIG. 1.

The imaging device 1 comprises an X-ray source 3 which irradiates a subject M with X-rays and a radiation detector 5 which detects X-rays passing through the subject M and acquires a radiographic image of the subject M.

The radiation detector 5 can repeatedly perform a process of recording and reading a radiographic image and may be a so-called direct radiation detector which directly receives radiation and generates charge or a so-called indirect radiation detector which converts radiation into visible light and converts the visible light into a charge signal. In addition, as a method for reading a radiographic image signal, it is preferable to use a so-called thin film transistor (TFT) reading method which turns on and off a TFT switch to read a radiographic image signal or a so-called optical reading method which emits reading light to read a radiographic image signal. However, the invention is not limited thereto. Other methods may be used. In the radiation detector 5, logarithmic conversion and A/D conversion are performed for a charge signal. Therefore, in a radiographic image that is output from the radiation detector 5, the value of each pixel has a linear relationship with the logarithmic amount of radiation.

Figure 2:
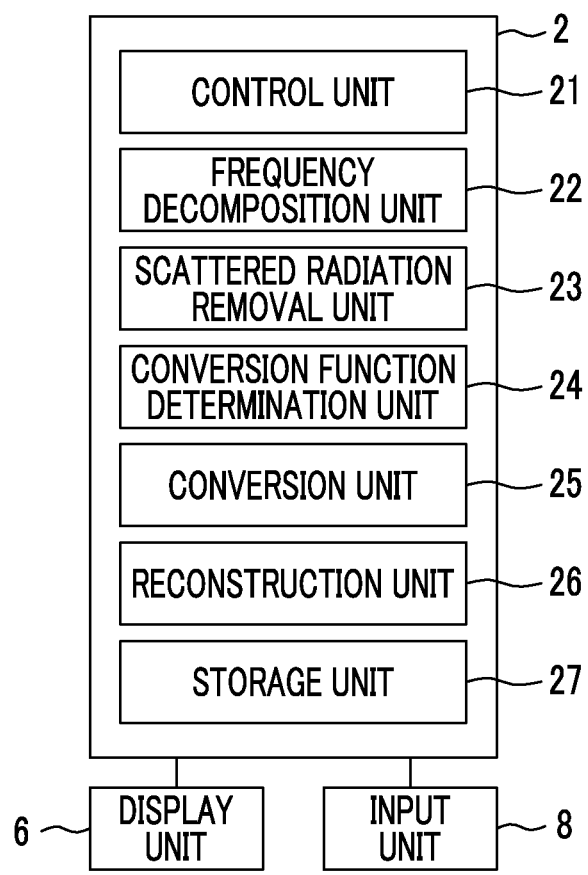
FIG. 2 is a block diagram schematically illustrating the internal structure of a computer of the radiography system according to the first embodiment.

The computer 2 comprises, for example, a central processing unit (CPU), a semiconductor memory, a communication interface, and a storage device, such as a hard disk or an SSD. A control unit 21, a frequency decomposition unit 22, a scattered radiation removal unit 23, a conversion function determination unit 24, a conversion unit 25, a reconstruction unit 26, and a storage unit 27 forming the radiographic image processing device are implemented by these hardware components, as illustrated in FIG. 2.

The control unit 21 controls the capture of an image by the X-ray source 3 and the radiation detector 5, controls the reading of a radiographic image from the radiation detector 5, or controls all of the processes performed in the computer 2.

The frequency decomposition unit 22 performs frequency decomposition for a radiographic image (hereinafter, referred to as a first radiographic image) acquired from the radiation detector 5 to create a plurality of band images indicating frequency components in a plurality of different frequency bands.

The scattered radiation removal unit 23 performs inverse logarithmic conversion for the first radiographic image to acquire a radiographic image (hereinafter, referred to as a second radiographic image), calculates a scattered radiation component which is scattered by the subject M and is included in the second radiographic image, using the second radiographic image, and performs a scattered radiation removal process using the scattered radiation component to acquire a scattered-radiation-removed radiographic image.

The conversion function determination unit 24 determines a conversion function for converting the band image, according to the scattered radiation component included in the second radiographic image.

The conversion unit 25 converts the band image, using the conversion function, and generates a converted band image.

The reconstruction unit 26 reconstructs the scattered-radiation-removed radiographic image and the converted band image and acquires a processed radiographic image.

The storage unit 27 stores various kinds of information required for the scattered radiation removal process performed by the computer 2.

The display unit 6 is, for example, a CRT display or a liquid crystal display and assists the display of a captured radiographic image and various inputs required for image processing which will be described below. The input unit 8 is, for example, a keyboard, a mouse, or a touch panel.

The central processing unit executes a computer program stored in the storage unit 27 to implement the processes performed by the control unit 21, the frequency decomposition unit 22, the scattered radiation removal unit 23, the conversion function determination unit 24, the conversion unit 25, and the reconstruction unit 26. In addition, a plurality of processing devices which perform the processes of each unit may be provided in the computer 2.

Figure 3:
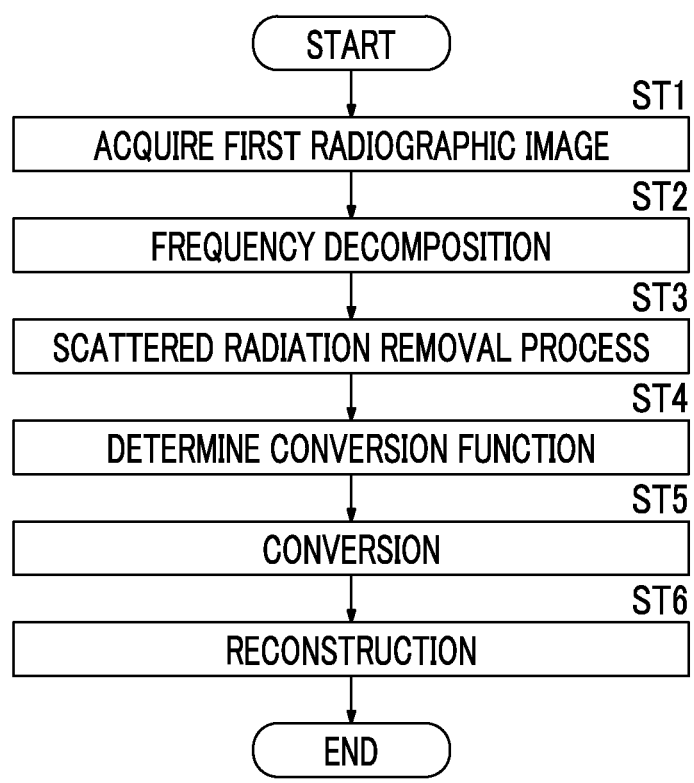
FIG. 3 is a flowchart illustrating a process which is performed in the first embodiment.
Figure 4:
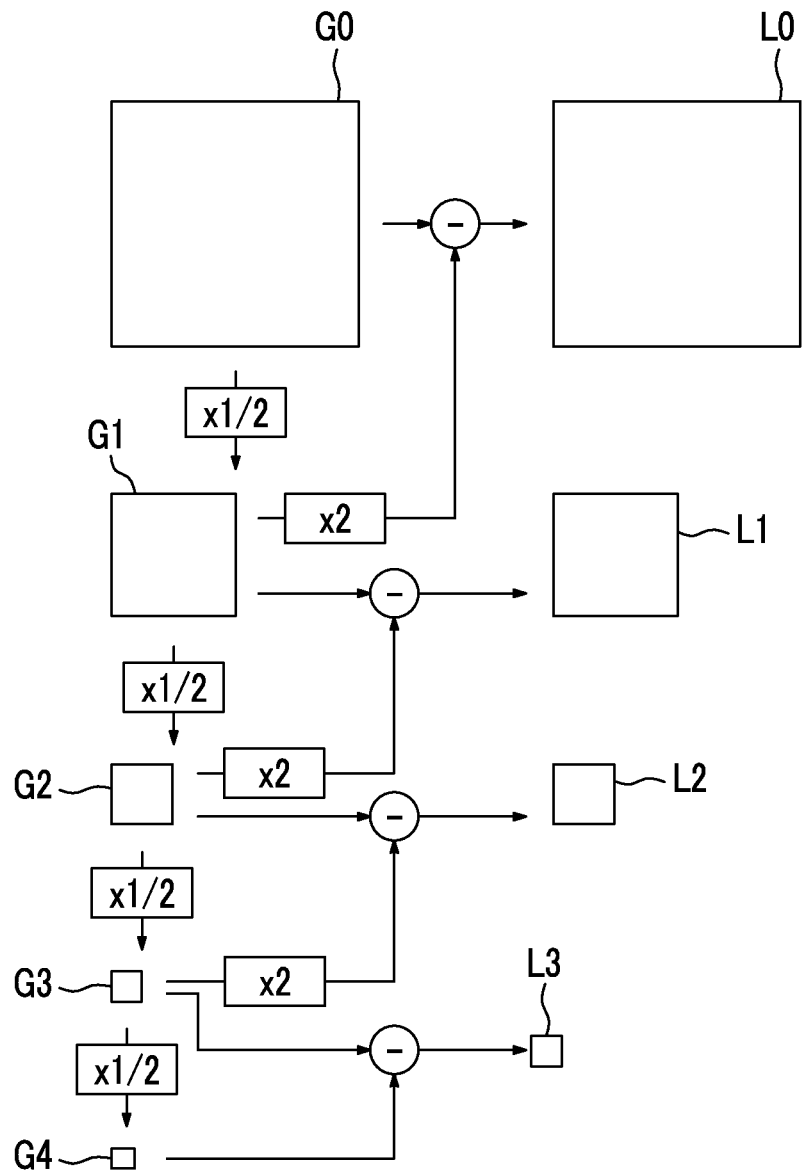
FIG. 4 is a diagram illustrating frequency decomposition.

Next, a process performed in the first embodiment will be described. FIG. 3 is a flowchart illustrating the process performed in the first embodiment. When a radiographic image of the subject M is captured and the control unit 21 of the computer 2 acquires a first radiographic image G0 in which a pixel value has a linear relationship with the logarithmic amount of radiation (Step ST1), the frequency decomposition unit 22 performs frequency decomposition for the first radiographic image G0 to generate a plurality of band images indicating a plurality of frequency components of the first radiographic image G0 (Step ST2). FIG. 4 is a diagram illustrating the frequency decomposition. First, the frequency decomposition unit 22 performs a filtering process using a Gaussian filter with σ=1 for the radiographic image G0 to reduce the radiographic image G0 by half and generates a Gaussian component G1. The Gaussian component G1 is obtained by reducing the radiographic image G0 by half. Then, the frequency decomposition unit 22 performs a known interpolation operation, such as cubic B-spline interpolation or linear interpolation, to enlarge the Gaussian component G1 so as to have the same size as the radiographic image G0, subtracts the enlarged Gaussian component G1 from the radiographic image G0, and generates a Laplacian component L0 which is a band image indicating a frequency component in the highest frequency band. In this embodiment, for convenience of explanation, the highest frequency band is referred to as a zeroth frequency band.

Then, the frequency decomposition unit 22 performs a filtering process using a Gaussian filter with σ=1 for the Gaussian component G1 to further reduce the Gaussian component G1 by half and generates a Gaussian component G2. Then, the frequency decomposition unit 22 enlarges the Gaussian component G2 so as to have the same size as the Gaussian component G1, subtracts the enlarged Gaussian component G2 from the Gaussian component G1 to generate a Laplacian component L1 which is a band image indicating a frequency component in a first frequency band. The frequency decomposition unit 22 repeats the above-mentioned process until a Laplacian component which is a band image in a desired frequency band is generated and generates Laplacian components Lj (j=0 to n) in a plurality of frequency bands. In this embodiment, the above-mentioned process is repeated until a Laplacian component L3 in a third frequency band and a Gaussian component G4 in a fourth frequency band are obtained.

Here, the signal value of each pixel in the Gaussian component indicates the density of each pixel and the signal value of the pixel in the Laplacian component indicates the size of a frequency component in the frequency band of the pixel. Therefore, in the following description, a Gaussian component in the fourth frequency band is referred to as a radiographic image G4. A plurality of band images in different frequency bands may be generated by other frequency decomposition methods such as wavelet conversion. In addition, frequency decomposition may be performed such that a Gaussian component and a Laplacian component having the same size as the original radiographic image G0 are acquired.

Figure 5:
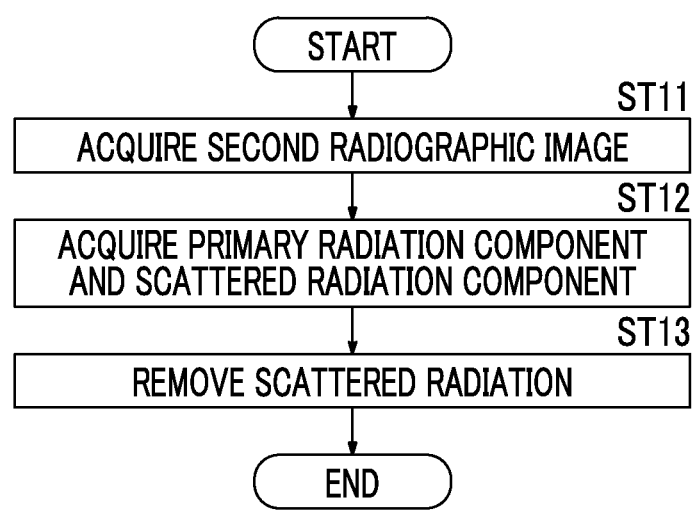
FIG. 5 is a flowchart illustrating a scattered radiation removal process according to the first embodiment.

Then, scattered radiation removal unit 23 performs the scattered radiation removal process using the Gaussian component in the fourth frequency band, that is, the radiographic image G4 (Step ST3). FIG. 5 is a flowchart illustrating the scattered radiation removal process.

In this embodiment, the frequency decomposition unit 22 performs frequency decomposition for the radiographic image G0 in which a pixel value has a linear relationship with the logarithmic amount of radiation. Therefore, the pixel value of the radiographic image G4 has a linear relationship with the logarithmic amount of radiation. The scattered radiation removal unit 23 performs inverse logarithmic conversion for the radiographic image G4 to generate a radiographic image GL4 (second radiographic image) in which the value of each pixel has a linear relationship with the amount of radiation (Step ST11). Here, a pixel value Tout of the radiographic image G4 has the following relation: $\log(\text{Iout})=\log(\text{Iin})+(-\mu t)$ (where Iin is an incident dose, μ is a linear attenuation coefficient corresponding to the composition of radiation, and t is a thickness). Therefore, $\text{Iout}=\text{Iin}\cdot e^{-\mu t}$ is established by the inverse logarithmic conversion.

Then, the scattered radiation removal unit 23 analyzes the radiographic image GL4 to acquire a primary radiation component and a scattered radiation component of the radiographic image GL4 (Step ST12). The radiographic image GL4 is analyzed on the basis of, for example, irradiation field information, subject information, and imaging condition when the radiographic image G0 is captured.

The irradiation field information is information indicating an irradiation field distribution related to the position and size of the irradiation field which is included in the radiographic image GL4 in a case in which imaging is performed using an irradiation field diaphragm. The subject information is information related to, for example, the position of the subject M on the radiographic image GL4, the distribution of the composition of the subject M, the size of the subject M, and the thickness of the subject M, in addition to the type of subject M, such as the chest, the abdomen, or the head. The imaging conditions include information related to, for example, an air gap (the distance from the subject M to the radiation detector 5) and the characteristics of the radiation detector 5, in addition to a tube voltage, an mAs value, and a source-image receptor distance (the sum of the distance from the X-ray source 3 to the subject M and the distance from the subject M to the radiation detector 5). The irradiation field information, the subject information, and the imaging conditions are factors for determining the distribution of the scattered radiation included in the radiographic image GL4. For example, the amount of scattered radiation depends on the magnitude of the irradiation field. As the thickness of the subject M increases, the amount of scattered radiation increases. If there is air between the subject M and the radiation detector 5, the amount of scattered radiation decreases. Therefore, the use of the above-mentioned information makes it possible to accurately acquire the primary radiation component and the scattered radiation component.

The scattered radiation removal unit 23 calculates the primary radiation component and the scattered radiation component from the distribution T(x, y) of the thickness of the subject in the radiographic image GL4 on the basis of the following Expressions (1) and (2).

$$Icp(x,y)=Io(x,y)\times\exp(-\mu\times T(x,y)) \quad (1)$$

$$Ics(x,y)=Io(x,y)*S\sigma(T(x,y)) \quad (2)$$

Here, (x, y) is the coordinates of a pixel position in the radiographic image GL4, Icp(x, y) is a primary radiation component at the pixel position(x, y), Ics(x, y) is a scattered radiation component at the pixel position(x, y), Io(x, y) is an incident dose on the surface of the subject at the pixel position(x, y), μ is a linear attenuation coefficient of the subject, and Sσ(T(x, y)) is a convolution kernel indicating scattering characteristics corresponding to the thickness of the subject at the pixel position(x, y). Expression (1) is based on a known exponential attenuation rule and Expression (2) is based on the method described in "J. M. Boon et al., An analytical model of the scattered radiation distribution in diagnostic radiolog, Med. Phys. 15(5), September/October 1988" (Reference Document 1).

The distribution T(x, y) of the thickness of the subject may be calculated by converting the pixel value of the radiographic image GL4 into a thickness, using the linear attenuation coefficient, on the assumption that a brightness distribution in the radiographic image GL4 is substantially identical to the distribution of the thickness of the subject M. For example, the value of water may be used as the linear attenuation coefficient value. Alternatively, the thickness of the subject M may be measured using, for example, a sensor or may be approximated by a model, such as a cube or an elliptic cylinder.

In Expression (2), * is an operator indicating a convolution operation. In this embodiment, * indicates a convolution operation for all of the pixels of the radiographic image GL4 at each pixel position(x, y). However, * may indicate a convolution operation for pixels in a region with a predetermined size. The properties of the operator change depending on, for example, the distribution of the irradiation field, the distribution of the composition of the subject M, and the imaging conditions (that is, the tube voltage, the mAs value, the source-image receptor distance, the air gap, and the characteristics of the radiation detector 5 during imaging), in addition to the thickness of the subject M. According to the method described in Reference Document 1, scattered radiation can be approximated by the convolution of a point spread function (Sσ(T(x, y)) in Expression (2)) with respect to the primary radiation. In addition, Sσ(T(x, y)) can be experimentally calculated on the basis of, for example, the irradiation field information, the subject information, the imaging conditions.

In this embodiment, Sσ(T(x, y)) may be calculated on the basis of the irradiation field information, the subject information, and the imaging conditions during imaging. A table in which various kinds of irradiation field information, various kinds of subject information, and various imaging conditions are associated with Sσ(T(x, y)) may be stored in the storage unit 27 and Sσ(T(x, y)) may be calculated on the basis of the irradiation field information, the subject information, and the imaging conditions during imaging, with reference to the table. In addition, Sσ(T(x, y)) may be approximated by T(x, y).

Here, the value of each pixel in the radiographic image GL4 is the sum of the primary radiation component and the scattered radiation component. It is preferable that a scattered radiation removal operation may be performed using the radiographic image G4 in which a pixel value has a linear relationship with the logarithmic amount of radiation. Therefore, the scattered radiation removal unit 23 calculates a conversion function S(x, y) for removing a scattered radiation in each pixel of the radiographic image GL4 from the primary radiation component and the scattered radiation component which are calculated on the basis of the above-mentioned Expressions (1) and (2), on the basis of the following Expression (3). The conversion function S(x, y) has a value of 0 to 1. Here, it is assumed that the conversion function S(x, y) indicates a scattered radiation content distribution in the radiographic image GL4.

$$S(x,y)=Icp(x,y)/(Ics(x,y)+Icp(x,y)) \quad (3)$$

The scattered radiation removal unit 23 multiplies the value G4(x, y) of each pixel of the radiographic image G4 before inverse logarithmic conversion by the conversion function S(x, y) on the basis of the following Expression (4) to calculate a scattered-radiation-removed radiographic image G4' (Step ST13) and ends the scattered radiation removal process.

$$G4'(x,y)=G4(x,y)\times S(x,y) \quad (4)$$

Since the conversion function S(x, y) has a value of 0 to 1, the pixel value of the radiographic image G4 is reduced by the multiplication of the radiographic image G4(x, y) by the conversion function S(x, y). As a result, the scattered radiation component is reduced. The conversion function determination unit 24 may calculate the conversion function S(x, y).

The scattered radiation removal unit 23 may subtract the scattered radiation component from the pixel value of the radiographic image GL4 to calculate a scattered-radiation-removed radiographic image GL4', as shown in the following Expression (5). In this case, the scattered radiation removal unit 23 performs logarithmic conversion for the radiographic image GL4' to acquire the scattered-radiation-removed radiographic image G4'.

$$GL4'(x,y)=GL4(x,y)-Ics(x,y) \quad (5)$$

Figure 6:
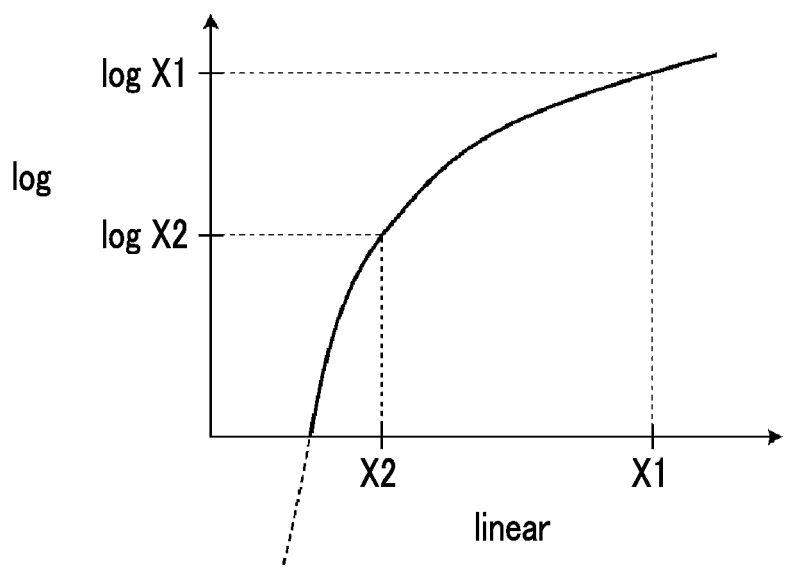
FIG. 6 is a graph illustrating the relationship between the amount of radiation and the logarithmic amount of radiation.

Returning to FIG. 2, the conversion function determination unit 24 determines a conversion function for converting the Laplacian components L0 to L3 (Step ST4). Next, the determination of the conversion function will be described. In this embodiment, the scattered radiation removal unit 23 performs inverse logarithmic conversion for the radiographic image G4 in which a pixel value has a linear relationship with the logarithmic amount of radiation to generate the radiographic image GL4 in which a pixel value has a linear relationship with the amount of radiation, calculates the primary radiation component Icp and the scattered radiation component Ics from the radiographic image GL4, and performs the scattered radiation removal process using the primary radiation component Icp and the scattered radiation component Ics. FIG. 6 is a graph illustrating the relationship between the amount of radiation and the logarithmic amount of radiation. In FIG. 6, the horizontal axis indicates the pixel value of a radiographic image which has a linear relationship with the amount of radiation and the vertical axis indicates the pixel value of a radiographic image which has a linear relationship with the logarithmic amount of radiation. The scattered radiation removal process represented by Expression (4) is synonymous with a scattered radiation removal process which subtracts the scattered radiation component Ics from the value of each pixel of the radiographic image GL4 which has a linear relationship with the amount of radiation, as shown in Expression (5). Here, when the value of a certain pixel is X1 and a pixel value after the scattered radiation component Ics is subtracted is X2, a pixel value is reduced from log X1 to log X2 in a radiographic image which has a linear relationship with the logarithmic amount of radiation, as illustrated in FIG. 6.

In the relationship illustrated in FIG. 6, gradients at the pixel values log X1 and log X2 on the logarithmic axis are 1/X1 and 1/X2, respectively, and X1>X2 is satisfied. Therefore, a change in the pixel value on the logarithmic axis is increased by the subtraction of the scattered radiation component. The conversion function determination unit 24 calculates a conversion function R(x, y) for converting the Laplacian components L0 to L3, using X1=Icp(x, y)+Isc(x, y) and X2=Icp(x, y), such that a change in the gradient is reflected, on the basis of the following Expression (6). Since X1>X2 is satisfied, the conversion function R(x, y) has a value that is greater than 1.

$$R(x,y)=(1/X2)/(1/X1)=X1/X2=(Ics(x,y)+Icp(x,y))/Icp(x,y) \quad (6)$$

In addition, the conversion function determination unit 24 calculates the conversion function R(x, y) for each pixel of the radiographic image G4 and creates a conversion function map. Since the resolution of the conversion function map is the same that of the radiographic image G4, the conversion function map is referred to as a conversion function map R4.

Then, the conversion unit 25 converts the Laplacian components L0 to L3, using the conversion function R(x, y) determined by the conversion function determination unit 24 (Step ST5). Here, the size of the conversion function map R4 determined by the conversion function determination unit 24 is half of the size of the Laplacian component L3. Therefore, the conversion function map R4 is enlarged two times by a known interpolation operation, such as cubic B-spline interpolation or linear interpolation, to create a conversion function map R3 having the same size as the Laplacian component L3. Similarly, a conversion function map R2 having the same size as the Laplacian component L2, a conversion function map R1 having the same size as the Laplacian component L1, and a conversion function map R0 having the same size as the Laplacian component L0 are generated.

Then, the conversion unit 25 converts the Laplacian component L0 to L3 and calculates converted Laplacian components L0' to L3', using the following Expression (7) (where j is in the range of 1 to 3).

$$Lj'(x,y)=Lj(x,y)\times Rj(x,y) \qquad (7)$$

Figure 7:
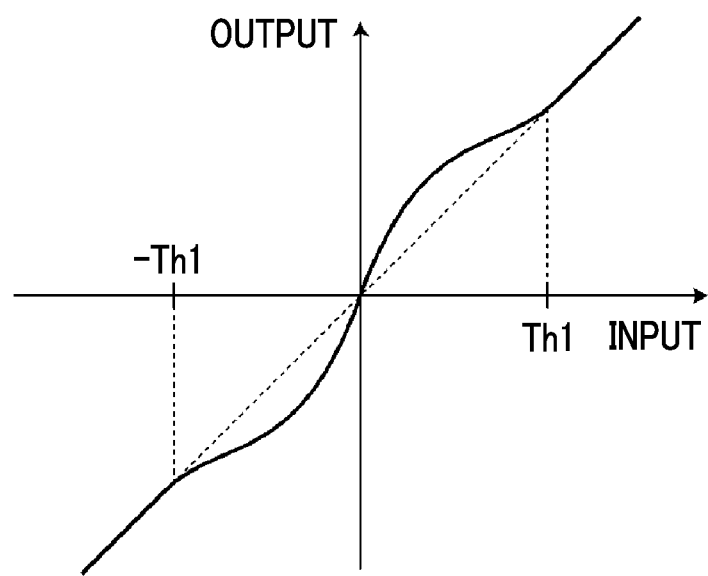
FIG. 7 is a diagram a conversion function for converting a band image such that a pixel value is suppressed.

However, since the subject M has a complicated body structure, such as a lung field, a bone, muscle, and fat, in some cases, it is difficult to accurately calculate the scattered radiation component. In this case, in a case in which the conversion function R(x, y) is used to convert the Laplacian component, a structure with high contrast, such as metal included in a bone or a medical treatment tool, is likely to be over-enhanced. As such, when contrast is over-enhanced, for example, an artifact is generated in the structure, which results in the deterioration of the quality of the radiographic image. Therefore, when the absolute value of the value of the Laplacian component is greater than a predetermined threshold value, the conversion function R(x, y) may be determined such that the value is suppressed. For example, as illustrated in FIG. 7, the conversion function R(x, y) may be determined such that, as the absolute value of the Laplacian component, which is an input value, becomes closer to a threshold value Th1, the value becomes non-linearly closer to 1 and, when the absolute value is greater than the threshold value Th1, the input value is converted without any change.

Figure 8:
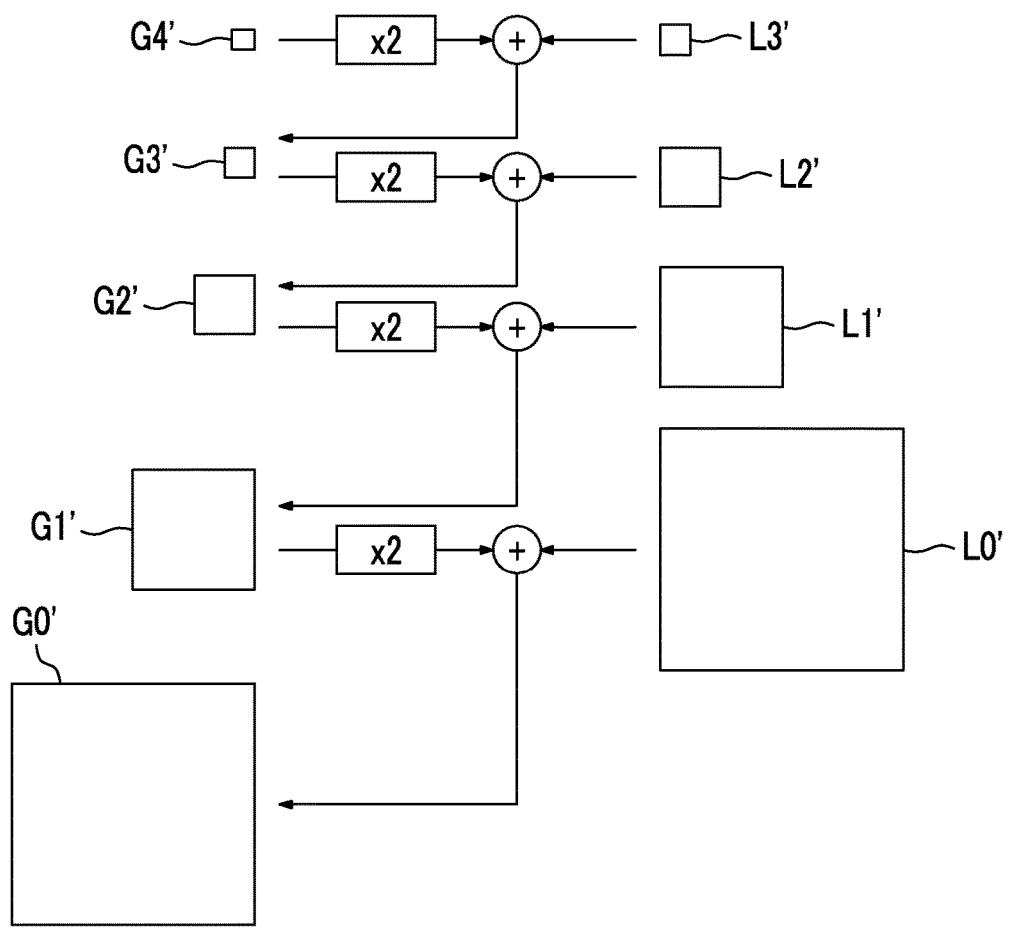
FIG. 8 is a diagram illustrating reconstruction.

Then, the reconstruction unit 26 reconstructs the scattered-radiation-removed radiographic image G4' (that is, a Gaussian component in the lowest frequency band) and the converted Laplacian components L0' to L3' to generate a processed radiographic image G0' (Step ST6) and ends the process. FIG. 8 is a diagram illustrating the reconstruction. First, in a case in which the scattered-radiation-removed radiographic image is a radiographic image GL4', the reconstruction unit 26 performs logarithmic conversion for the radiographic image GL4' to generate the radiographic image G4'. Then, the reconstruction unit 26 enlarges the radiographic image G4' so as to have the same size (that is, two times) as the converted Laplacian component L3', using an interpolation operation, and adds the enlarged radiographic image G4' to the converted Laplacian component L3' to generate the converted Gaussian component G3'.

Then, the reconstruction unit 26 enlarges the converted Gaussian component G3' so as to have the same size as the converted Laplacian component L2' and adds the enlarged radiographic image G3' and the converted Laplacian component L2' to generate the converted Gaussian component G2'. Then, the above-mentioned process is repeated until the converted Laplacian component G0' in the highest frequency band, that is, the processed radiographic image G0' is generated.

Here, since a pixel value has a linear relationship with the amount of radiation in the radiographic image GL4 for calculating the scattered radiation component, it is possible to accurately the scattered radiation component. As a result, it is possible to accurately remove the scattered radiation component from the radiographic image GL4 or the radiographic image G4. Since the conversion function R(x, y) is calculated from the scattered radiation component of the radiographic image GL4 which has a linear relationship with the amount of radiation, it is possible to accurately enhance a Laplacian component, using the conversion function R(x, y). Therefore, in a reconstructed radiographic image, scattered radiation is removed and a high-frequency component included in the radiographic image G0 is enhanced. In the processed radiographic image G0', a reduction in contract caused by scattered radiation is prevented.

In particular, since a pixel value has a linear relationship with the logarithmic amount of radiation in the radiographic image G0, it is possible to easily determine the conversion function R(x, y) from the scattered radiation component. In addition, the conversion of the Laplacian component by the conversion function R(x, y) makes it possible to effectively enhance the Laplacian component. Therefore, it is possible to effectively prevent a reduction in contrast caused by the scattered radiation of the radiographic image with high accuracy.

In the first embodiment, a scattered radiation component is calculated from the radiographic image GL, which is a Gaussian component in the lowest frequency band, and a conversion function map is created. However, a filtering process using a low-pass filter may be performed for the radiographic image G0 to gradate the radiographic image G0, inverse logarithmic conversion may be performed for the gradated radiographic image G0 to acquire a radiographic image GL0 in which a pixel value has a linear relationship with the amount of radiation, and a primary radiation component and a scattered radiation component may be calculated from the radiographic image GL0. In this case, the created conversion function map has the same size as the original radiographic image G0, that is, the Laplacian component L0. Therefore, the conversion function determination unit 24 may reduce the conversion function map (which is referred to as R0 similarly to the above) having the same size as the Laplacian component L0 by half to create a conversion function map R1 having the same size as the Laplacian component L1. Similarly, a conversion function map R2 having the same size as the Laplacian component L2 and a conversion function map R3 having the same size as the Laplacian component L3 may be generated. In addition, the scattered radiation removal unit 23 may calculate a conversion function C, using the primary radiation component and the scattered radiation component calculated from the radiographic image GL0, and may perform the scattered radiation removal process for the radiographic image G4.

In the first embodiment, the Laplacian components in all of the frequency bands are converted by the conversion function. However, at least one of the Laplacian components may be converted by the conversion function. In this case, the conversion function may be determined only for the Laplacian component in the frequency band to be converted.

Figure 9:
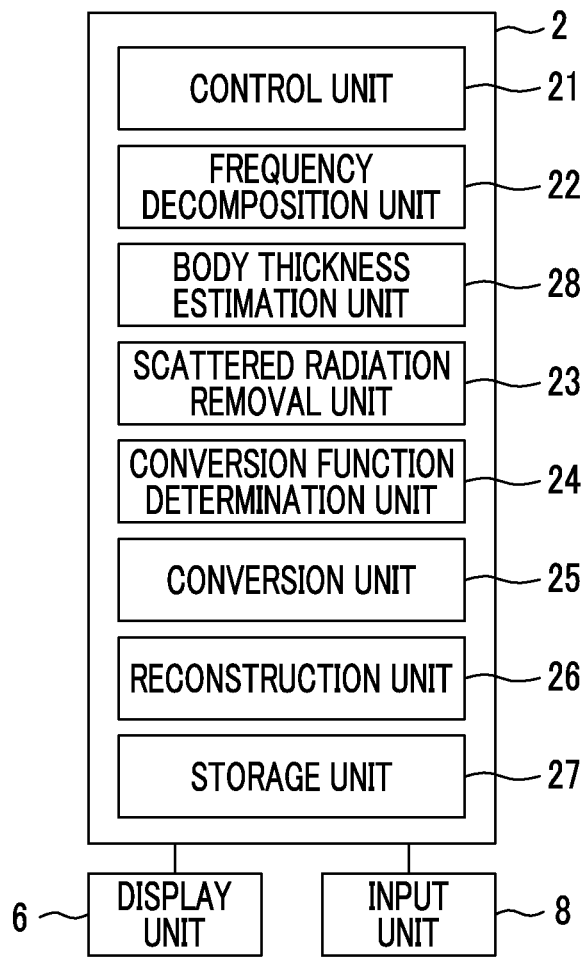
FIG. 9 is a block diagram schematically illustrating the internal structure of a computer of a radiography system according to a second embodiment.

Next, a second embodiment of the invention will be described. FIG. 9 is a block diagram schematically illustrating the internal structure of a computer in a radiography system according to the second embodiment of the invention. As illustrated in FIG. 9, the second embodiment differs from the first embodiment in that it comprises a body thickness estimation unit 28 which analyzes a radiographic image to estimate a body thickness distribution of a subject M and the body thickness estimated by the body thickness estimation unit 28 is used as a body thickness which is used to calculate a scattered radiation component of the radiographic image GL4.

Figure 10:
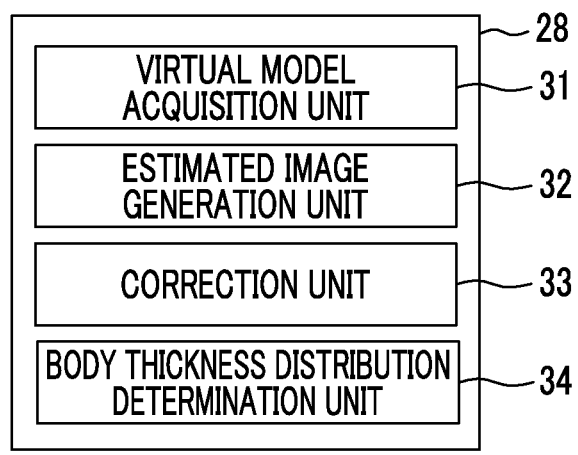
FIG. 10 is a block diagram schematically illustrating the structure of a body thickness estimation unit.

FIG. 10 is a block diagram schematically illustrating the structure of the body thickness estimation unit. As illustrated in FIG. 10, the body thickness estimation unit 28 comprises a virtual model acquisition unit 31, an estimated image generation unit 32, a correction unit 33, and a body thickness distribution unit 34.

The virtual model acquisition unit 31 acquires a virtual model K of the subject M having an initial body thickness distribution $T_0$ (predetermined body thickness distribution).

The estimated image generation unit 32 generates a composite image of an estimated primary radiation image Ip, which is obtained by estimating a primary radiation image obtained by radiography of the virtual model, and an estimated scattered radiation image Is, which is obtained by estimating a scattered radiation image obtained by radiography of the virtual model, as an estimated image Im which is obtained by estimating a radiographic image obtained by radiography of the subject M, on the basis of the virtual model K.

The correction unit 33 corrects the initial body thickness distribution $T_0$ of the virtual model K such that the difference between the estimated image Im and the radiographic image GL4 is reduced, on the basis of the estimated image Im and the radiographic image GL4.

The body thickness distribution determination unit 34 determines a corrected body thickness distribution Tn−1 (n is a natural number) as the body thickness distribution Tk of the radiographic image GL4.

In the second embodiment, a storage unit 27 stores the virtual model K of the subject M having the initial body thickness distribution $T_0$ (x, y). The body thickness means the total thickness of a subject region except for an air region on the path of the emitted radiation.

Figure 11:
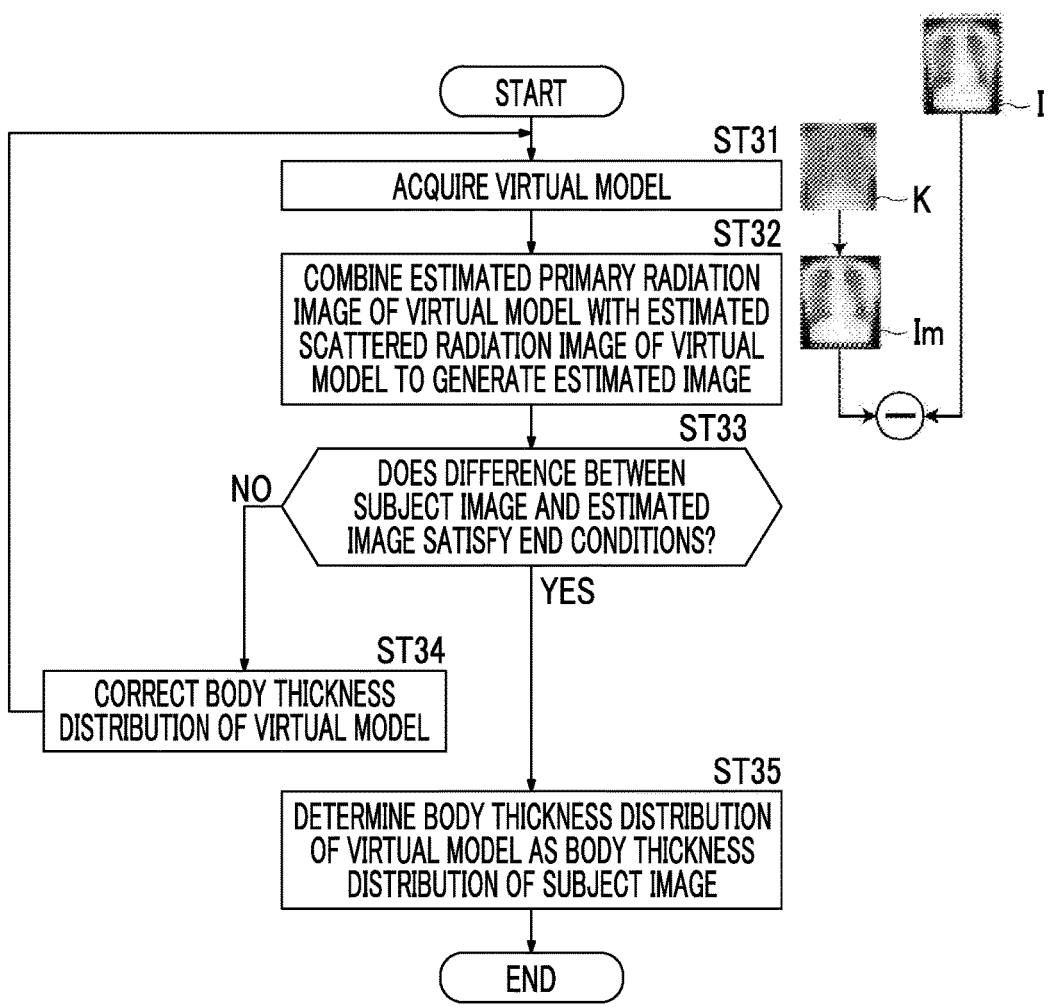
FIG. 11 is a flowchart illustrating a body thickness estimation process.

Next, a body thickness estimation process will be described. FIG. 11 is a flowchart illustrating the body thickness estimation process. The virtual model acquisition unit 31 of the body thickness estimation unit 28 acquires the virtual model K of the subject M having the initial body thickness distribution $T_0$ (x, y) from the storage unit 27 (Step ST31). The virtual model K is data which virtually indicates the subject M and in which a body thickness that follows the initial body thickness distribution $T_0$ (x, y) is associated with each position on an x-y plane. In addition, structures (here, anatomic structures such as a lung field, a bone, and an organ) included in the virtual model K, the arrangement of the structures, and characteristic information indicating, for example, the characteristics of the structures with respect to radiation are set on the basis of the arrangement and composition of anatomic structures, such as the lung field of the chest and abdomen of a comparative subject and the bones.

Figure 12:
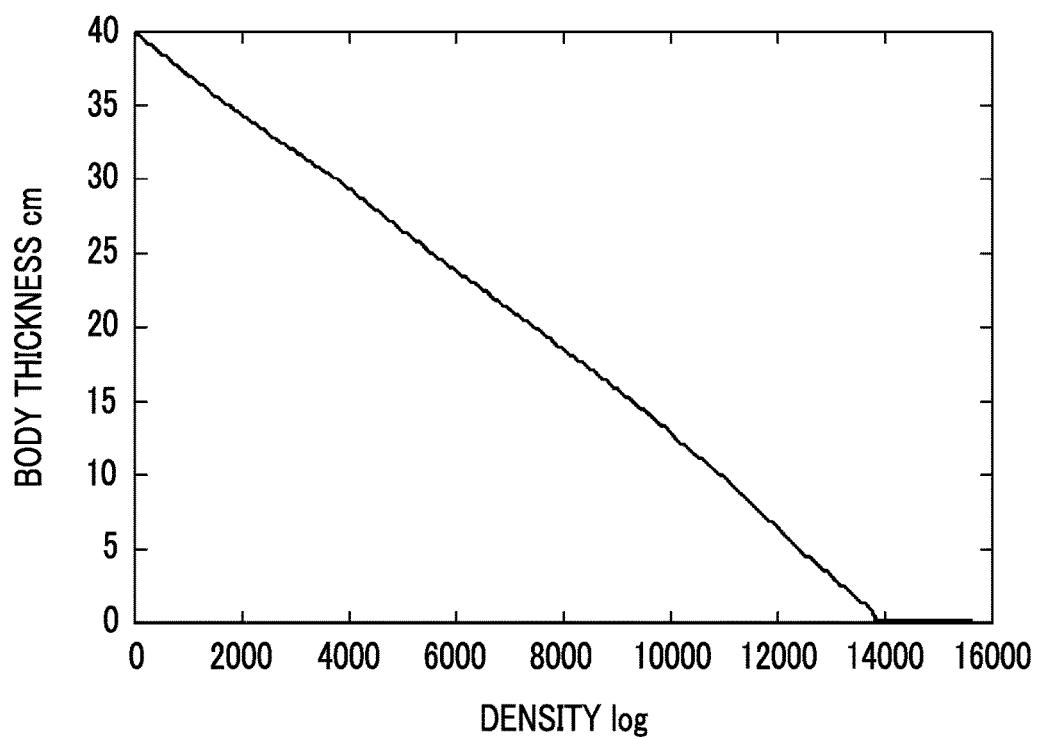
FIG. 12 is a diagram illustrating an example of a body thickness distribution correspondence table.

The virtual model K may have any initial body thickness distribution $T_0$ (x, y). However, in this embodiment, the initial body thickness distribution $T_0$ is generated and acquired by the virtual model acquisition unit 31. The virtual model acquisition unit 31 acquires imaging conditions, such as the radiation dose of the subject M, a tube voltage, and an SID, and acquires a table in which the pixel value corresponding to the imaging conditions of the subject M is associated with the body thickness from the storage unit 27. FIG. 12 illustrates an example of the table in which the pixel value is associated with the body thickness. Then, the virtual model acquisition unit 31 specifies the body thickness corresponding to the value of each pixel in the radiographic image GL4 of the subject M on the basis of the table illustrated in FIG. 12 to acquire the body thickness distribution of the radiographic image GL4. Then, the virtual model acquisition unit 31 acquires the body thickness distribution of the radiographic image GL4 as the initial body thickness distribution $T_0$ (predetermined body thickness distribution) of the virtual model K. The initial body thickness distribution $T_0$ may be generated during the process of acquiring the virtual model K or may be set in advance before the process of acquiring the virtual model K. The above-mentioned process is represented by the following Expression (11). In addition, I(x, y) indicates the value of each pixel in the radiographic image GL4 and $T_0$ (x, y) indicates an initial body thickness distribution at each pixel position.

$$T_0(x,y) = \text{LUT}(I(x,y)) \quad (11)$$

Figure 13:
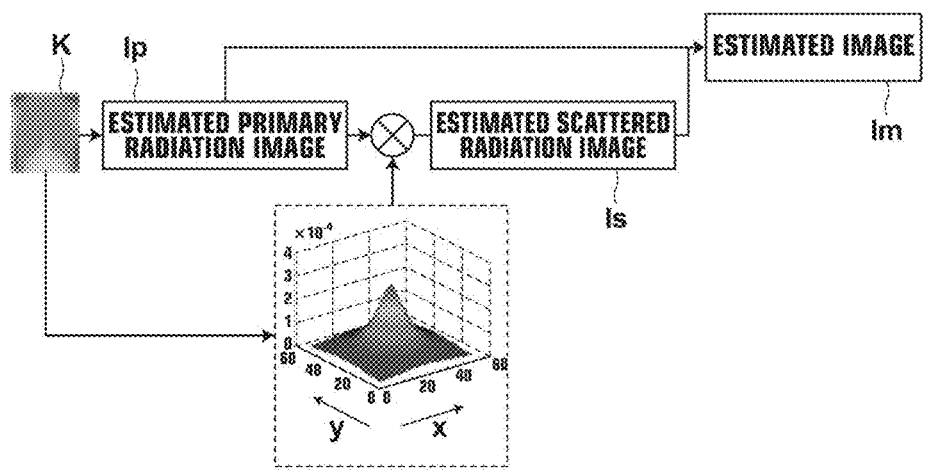
FIG. 13 is a diagram illustrating an example of an estimated image generation method.
Figure 14:
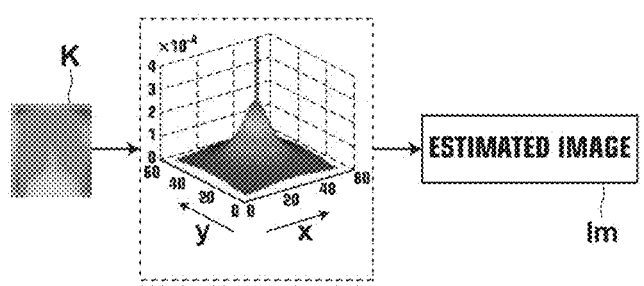
FIG. 14 is a diagram illustrating another example of the estimated image generation method.

Then, the estimated image generation unit 32 combines an estimated primary radiation image Ip, which is obtained in a case in which the image of the virtual model K is captured under the same imaging conditions as the radiographic image G0 from which the radiographic image GL4 is acquired, and an estimated scattered radiation image Is, which is obtained in a case in which the image of the virtual model K is captured under the same imaging conditions as the radiographic image G0, to generate an estimated image Im (Step ST32). FIGS. 13 and 14 are diagrams illustrating a method for generating the estimated image Im.

As illustrated in FIG. 13, the estimated image generation unit 32 generates the estimated primary radiation image Ip, which is obtained in a case in which the image of the virtual model K is captured under the same imaging conditions as the radiographic image GL4, according to the following Expression (12), and generates the estimated scattered radiation image Is using the generated estimated primary radiation image Ip, according to the following Expression (13). Then, the estimated image generation unit 32 combines the estimated primary radiation image Ip and the estimated scattered radiation image Is to generate the estimated image Im, as shown in the following Expression (14) (Step ST32). When the estimated primary radiation image Ip and the estimated scattered radiation image Is are generated first, the initial body thickness distribution $T_0$ (x, y) is used in Estimation Expressions (12) and (13) (n is 1 in Expressions (12) and (13)).

$$I_p(x, y) = I_o(x, y) \times \exp(-T_{n-1}(x, y) \times \mu) \quad (12)$$

$$I_s(x, y) = \sum_{x',y'} I_p(x', y') K_s(x, y, T_{n-1}(x', y'), \theta_{x',y'}) \quad (13)$$

$$I_m(x, y) = I_p(x, y) + I_s(x, y) \quad (14)$$

Here, (x, y) is the coordinates of a pixel position in the radiographic image GL4, Ip(x, y) is an estimated primary radiation image at the pixel position (x, y), Is(x, y) is an estimated scattered radiation image at the pixel position (x, y), Io(x, y) is a dose at the pixel position (x, y), Im(x, y) is an estimated image at the pixel position (x, y), μ is a linear attenuation coefficient of the subject M, and Ks(x, y, Tn(x', y'), θx', y') is a convolution kernel indicating a point spread function corresponding to the thickness of the subject at the pixel position (x, y). The dose Io(x, y) is a radiation dose which is detected by the radiation detector 5 on the assumption that no subject is present and varies depending on the distance (SID) between the X-ray source 3 and a detection surface of the radiation detector 5, a tube voltage, and an mAs value. In addition, θx', y' indicates a parameter which is specified by the imaging conditions, such as the tube voltage, or the characteristic information of the virtual model K.

In addition, the estimated image Im may be an image which is estimated to be obtained in a case in which a radiographic image of the virtual model K is captured and may be any image which is substantially regarded as a composite image of the estimated primary radiation image Ip and the estimated scattered radiation image Is. For example, as illustrated in FIG. 14, the estimated image Im may be generated by the convolution integral of a kernel combining a primary radiation component and a scattered component, using the following Expression (15), instead of Expressions (12) to (14). Here, Kp+s(x, y, Tn−1(x', y'), θx', y') is a kernel indicating a point spread function that combines the primary radiation component and the scattered component. In addition, any model function may be used as long as it can generate an estimated image obtained by combining the estimated primary radiation image and the estimated scattered radiation image from the image obtained by radiography.

In addition, Ks(x, y, Tn(x', y'), θx', y') and Kp+s(x, y, Tn−1(x', y'), θx', y') can be experimentally calculated according to, for example, imaging conditions.

In this embodiment, the kernels Ks(x, y, Tn(x', y'), θx', y') and Kp+s(x, y, Tn−1(x', y'), θx', y') may be calculated on the basis of the imaging conditions during imaging. A table in which various imaging conditions and the kernels Ks(x, y, Tn(x', y'), θx', y') and Kp+s(x, y, Tn−1(x', y'), θx', y') are associated with each other is stored in the storage unit 27 and the kernels Ks(x, y, Tn(x', y'), θx', y') and Kp+s(x, y, Tn−1(x', y'), θx', y') are calculated on the basis of irradiation field information, subject information, and imaging conditions during imaging, with reference to the table.

$$I_m(x, y) = \sum_{x', y'} K_{p+s}(x, y, T_{n-1}(x', y'), \theta_{x', y'}) \quad (15)$$

The next process will be described with reference to the flowchart illustrated in FIG. 11. Then, the body thickness distribution determination unit 34 determines whether the difference between the radiographic image GL4 and the estimated image Im satisfies end conditions (Step ST33). Here, the following error value $V_{error}$ indicating the difference between the radiographic image GL4 and the estimated image Im is defined as shown in Expressions (16) and (17). It is determined whether the error value $V_{error}$ is equal to or less than a threshold value as the end conditions. As shown in Expression (17), the sum of the squares of each pixel value of a difference image which is obtained by subtracting the estimated image Im from the radiographic image GL4 is defined as an error function $F_{error}$. In addition, any determination method may be used as long as it can determine whether or not the difference between the radiographic image GL4 and the estimated image Im is small enough to be allowed, as the end conditions.

$$V_{error} = f_{error}(I_m(x, y), I(x, y)) \quad (16)$$

$$f_{error}(I_m(x, y), I(x, y)) = \sum_{x,y} (I_m(x, y) - I(x, y))^2 \quad (17)$$

However, the invention is not limited to the above-mentioned example. For example, the error function $F_{error}$ can be defined by any method which can indicate the difference between the radiographic image GL4 and the estimated image Im. For example, as shown in the following Expression (18), the sum of the absolute values of each pixel value of the differential image obtained by subtracting the estimated image Im from the radiographic image GL4 may be defined as the error function $F_{error}$.

$$f_{error}(I_m(x, y), I(x, y)) = \sum_{x,y} |I_m(x, y) - I(x, y)| \quad (18)$$

In a case in which the error value $V_{error}$ does not satisfy the end conditions (Step ST33; No), the body thickness distribution determination unit 34 performs a correction process of correcting a body thickness distribution Tn−1 (the initial body thickness distribution $T_0$ in a case in which n is 1) (Step ST34).

Any method which can acquire the correction value of each position in the body thickness distribution Tn−1 such that the difference between the radiographic image GL4 and the estimated image Im is reduced can be applied in order to perform the process of correcting the body thickness distribution Tn−1. In this embodiment, a process is performed which changes the body thickness distribution Tn−1 of the virtual model K for each partial region including one or more pixels in the virtual model K to calculate the body thickness of the partial region where the difference between the estimated image Im and the radiographic image GL4 is small. Then, the body thickness distribution of the virtual model K is corrected using the calculated body thickness of each partial region.

Specifically, in this embodiment, it is assumed that the correction value of the body thickness with the body thickness distribution Tn−1 is calculated using the steepest descent method. It is possible to minimize the output value of the error function $F_{error}$ by repeatedly calculating dTn−1(x, y) on the basis of the primary partial differential (gradient) of the error function $F_{error}$ while changing only the body thickness at one specific coordinate point in Tn−1(x, y) among the pixels of the virtual model K, using the following Expressions (19) and (20). Then, the body thickness at one specific coordinate point when the output value of the error function $F_{error}$ is minimized is determined as the correction value of the body thickness at the specific coordinate point. For the other pixels, similarly, the correction value of each body thickness is calculated and the body thickness distribution of each pixel is corrected. In this way, a corrected body thickness distribution Tn is acquired.

$$T_n(x, y) = T_{n-1}(x, y) - \alpha dT_{n-1}(x, y) \quad (19)$$
$$= T_{n-1}(x, y) - \alpha \frac{d}{dT_{n-1}(x, y)} f_{error}$$

$$\frac{d}{dT_{n-1}(x, y)} f_{error} = \quad (20)$$
$$\sum_{x', y'} (I_m(x', y') - I(x', y')) \frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) = \quad (21)$$
$$K_{p+s}(x', y', T_{n-1}(x, y), +dt, \theta_{x,y}) - K_{p+s}(x', y', T_{n-1}(x, y), \theta_{x,y})$$

However, in Expression (19), α is an update coefficient which is a parameter indicating the update speed of the body thickness. As an example of a method for calculating a differential value portion of Kp+s shown in Expression (20), for example, a value change when a very small value dt is added to Tn−1(x, y) can be calculated by Expression (21) and can be used as the value of Kp+s in the Expression (20). In Expressions (11) to (21), the same components are denoted by the same reference numerals and the description thereof will not be repeated. Any optimization method can be applied as long as it can minimize the error value $V_{error}$ indicating the difference between the radiographic image GL4 and the estimated image Im. For example, a simplex method, the steepest descent method, or a conjugate gradient method can be used.

When the corrected body thickness distribution Tn is acquired, the body thickness distribution determination unit 34 increases the value of n by 1 to update the value of n (n=n+1) and the virtual model acquisition unit 31 acquires the corrected body thickness distribution Tn (Step ST31). Then, the estimated image generation unit 32 and the body thickness distribution determination unit 34 perform the process from Step ST31 to Step ST33 for the acquired body thickness distribution Tn, using the same method as described above. Then, similarly, the process of correcting the body thickness distribution Tn (Step ST34), the process of acquiring the virtual model K having the corrected body thickness distribution Tn (Step ST31), the process of generating a new estimated image Im using the body thickness distribution Tn (Step ST32), and the process of determining whether the difference between the newly generated estimated image Im and the radiographic image GL4 satisfies the end conditions (Step ST33) are repeatedly performed until the error value $V_{error}$ indicating the difference between the radiographic image GL4 and the estimated image Im satisfies the end conditions.

On the other hand, in a case in which it is determined that the error value $V_{error}$ satisfies the end conditions (Step ST33: Yes), the body thickness distribution determination unit 34 determines the body thickness distribution Tn which is used for the error value $V_{error}$ when the end conditions are satisfied as the body thickness distribution Tk of the radiographic image GL4 and ends the body thickness estimation process (Step ST35).

In the second embodiment, the body thickness estimation unit 28 calculates the primary radiation component Icp and the scattered radiation component Ics, using the estimated body thickness distribution Tn, on the basis of the above-mentioned Expressions (1) and (2), and performs the scattered radiation removal process, the determination of the conversion function, and the conversion and reconstruction of the Laplacian components, using the calculated primary radiation component Icp and scattered radiation component Ics, to acquire the processed radiographic image G0′, similarly to the first embodiment. Therefore, it is possible to appropriately remove the scattered radiation component, according to the estimated body thickness distribution, and thus to acquire a high-quality radiographic image.

Figure 15:
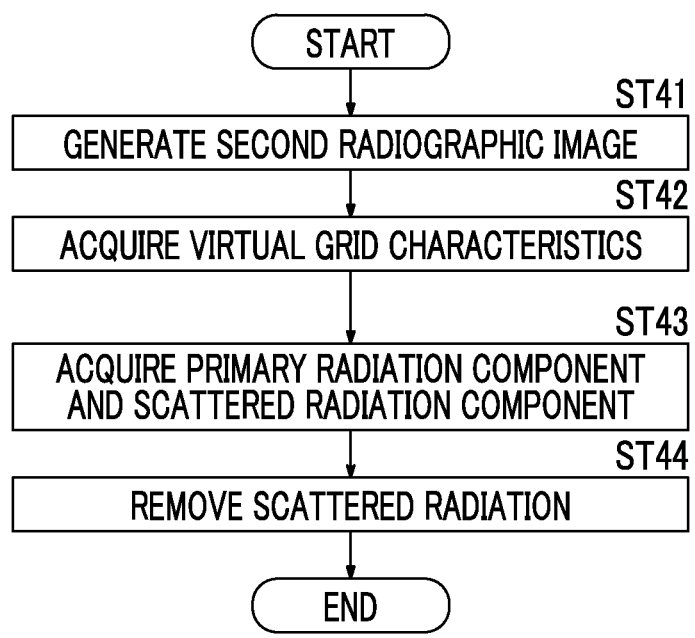
FIG. 15 is a flowchart illustrating a scattered radiation removal process according to a third embodiment.

In the first and second embodiments, during the scattered radiation removal process, virtual grid characteristics, which are the characteristics of a virtual grid that is assumed to be used in order to remove scattered radiation when a radiographic image is captured, may be acquired and the scattered radiation removal process may be performed for the radiographic image on the basis of the virtual grid characteristics. Next, the scattered radiation removal process using the virtual grid characteristics will be described as a third embodiment. FIG. 15 is a flowchart illustrating a process performed in the third embodiment. Similarly to the first embodiment, the scattered radiation removal unit 23 performs inverse logarithmic conversion for the radiographic image G4 to generate the radiographic image GL4 in which the value of each pixel has a linear relationship with the amount of radiation (Step ST41). Then, the scattered radiation removal unit 23 acquires virtual grid characteristics, which are the characteristics of a virtual grid that is assumed to be used in order to remove scattered radiation when a radiographic image is captured, in order to remove the influence of scattered radiation from the radiographic image GL4 (Step ST42). In this embodiment, the virtual grid characteristics include scattered radiation transmittance Ts for the virtual grid and the transmittance (primary radiation transmittance) Tp of primary radiation which passes through the subject M and is directly emitted to the radiation detector 5. In addition, the values of the scattered radiation transmittance Ts and the primary radiation transmittance Tp are in the range of 0 to 1.

The scattered radiation removal unit 23 may directly receive the values of the scattered radiation transmittance Ts and the primary radiation transmittance Tp from the input unit 8 to acquire the virtual grid characteristics. In this embodiment, the scattered radiation removal unit 23 acquires the virtual grid characteristics, that is, the scattered radiation transmittance Ts and the primary radiation transmittance Tp, on the basis of the imaging conditions. In the former case, the input unit 8 corresponds to characteristic acquisition means. In the latter case, the control unit 21 corresponds to the characteristic acquisition means.

The imaging conditions for acquiring the virtual grid characteristics include at least one of a source-image receptor distance (SID) during imaging, a tube voltage, an mAs value (tube current-time product), the target of a radiation source, a material forming a filter, or the type of radiation detector used for imaging. Here, when a radiographic image is captured, the type of grid used is determined according to the imaging conditions. In addition, the type of grid varies depending on, for example, a grid ratio, grid density, information indicating whether the grid is a convergence type or a parallel type, a focusing distance in a case in which the grid is a convergence type, and an interspace material (for example, aluminum, fiber, or Bakelite). The scattered radiation transmittance Ts and the primary radiation transmittance Tp vary depending on the type of grid. Therefore, in this embodiment, a table in which various imaging conditions are associated with the virtual grid characteristics is stored in the storage unit 27. The scattered radiation removal unit 23 acquires the virtual grid characteristics from the imaging conditions with reference to the table.

Then, similarly to the first embodiment, the scattered radiation removal unit 23 acquires a primary radiation component and a scattered radiation component of the radiographic image GL4 (Step ST43). Then, the scattered radiation removal unit 23 calculates a conversion function Q(x, y) for each pixel of the radiographic image GL4 before inverse logarithmic conversion from the scattered radiation transmittance Ts and the primary radiation transmittance Tp, which are the virtual grid characteristic, and the conversion function calculated by the above-mentioned Expression (3), that is, a scattered radiation content distribution S(x, y), using the following Expression (22).

$$Q(x,y)=S(x,y)\times Ts+(1-S(x,y))\times Tp \qquad (22)$$

Since each of the scattered radiation transmittance Ts, the primary radiation transmittance Tp, and the scattered radiation content distribution S(x, y) has a value of 0 to 1, the conversion function Q(x, y) also has a value of 0 to 1. The scattered radiation removal unit 23 performs a scattered radiation removal process by multiplying each pixel value G4(x, y) of the radiographic image G4 by the conversion function Q(x, y), using the following Expression (23) and calculates a radiographic image G4' from which scattered radiation has been removed (Step ST44). Then, the scattered radiation removal unit 23 ends the scattered radiation removal process.

$$G4'(x,y)=G4(x,y)\times Q(x,y) \quad (23)$$

As such, in the third embodiment, the scattered radiation removal process is performed using the virtual grid characteristics. Therefore, it is possible to obtain the same scattered radiation removal effect as that when imaging is performed using the grid that is assumed to be used.

In the third embodiment, the scattered radiation transmittance Ts and the primary radiation transmittance Tp are acquired as the virtual grid characteristics. However, only one of the scattered radiation transmittance Ts and the primary radiation transmittance Tp may be acquired.

In the third embodiment, the radiographic image G0 which is obtained by imaging using a grid may be a processing object. In this case, a process of removing a stripe pattern caused by the grid is performed for the radiographic image G0 and then the scattered radiation removal process is performed for the radiographic image G0. The scattered radiation removal process may acquire a radiographic image (first grid usage image) captured using a first grid, which is a desired grid, acquire virtual grid characteristics corresponding to a desired virtual grid, and convert the amount of scattered radiation and the amount of primary radiation in the acquired first grid usage image into the amount of scattered radiation and the amount of primary radiation which correspond to grid (a grid having the scattered radiation transmittance and the primary radiation transmittance which are the acquired virtual grid characteristics) corresponding to the acquired virtual grid characteristics. In addition, one of the first grid and the grid corresponding to the virtual grid characteristics may have a larger scattered radiation removal effect and the first grid and the grid corresponding to the virtual grid characteristics may be arbitrarily selected according to purposes and circumstances. As the process of removing a stripe pattern caused by the grid, for example, the method disclosed in JP2012-203504A can be used.

In addition, the scattered radiation removal process according to the third embodiment may be performed for a processed radiographic image obtained by a scattered radiation removal process which applies one virtual grid characteristic (first virtual grid characteristic) to a radiographic image captured without using a grid. In this case, the first virtual grid characteristic and a first processed radiographic image, which is the processed radiographic image to which the first virtual grid characteristic has been applied, may be acquired and a second virtual grid characteristic that is different from the first virtual grid characteristic and corresponds to a desired virtual grid may be acquired. Then, the amount of scattered radiation and the amount of primary radiation in the first processed radiographic image may be converted into the amount of scattered radiation and the amount of primary radiation corresponding to the second virtual grid characteristic on the basis of the second virtual grid characteristic. In addition, one of the first virtual grid characteristic and the second virtual grid characteristic may have a larger scattered radiation removal process and the first virtual grid characteristic and the second virtual grid characteristic may be arbitrarily selected according to purposes and circumstances.

The above-mentioned processes make it possible to virtually acquire a processed radiographic image that seems to be captured, using a grid having a grid ratio of 10:1, which is different from the grid used, on the basis of the radiographic image which is captured using a grid having a grid ratio of 3:1 (or the first processed radiographic image obtained by performing the scattered radiation removal process for the radiographic image captured without using a grid, on the basis of the first virtual grid characteristic). Inversely, the above-mentioned processes make it possible to virtually acquire a processed radiographic image that seems to be captured, using the grid having a grid ratio of 3:1, which is different from the grid used, on the basis of the radiographic image which is captured using the grid having a grid ratio of 10:1 (or the first processed radiographic image obtained by performing the scattered radiation removal process for the radiographic image captured without using a grid, on the basis of the first virtual grid characteristic). In these cases, it is possible to easily acquire a radiographic image in which a grid ratio has been converted, without repeating a process of capturing the image of the subject M. Therefore, it is possible to obtain a processed radiographic image subjected to the scattered radiation removal process using a grid with a desired grid ratio from a radiographic image which has been captured at an unintended grid ratio or the first processed radiographic image. As a result, it is possible to respond to a demand for observing a processed radiographic image subjected to the scattered radiation removal process with different degrees, without re-capturing an image of the subject.

As a detailed method, a table in which Sσ indicating scattering characteristics in Expression (2) is associated with each combination of grid information before conversion that corresponds to a grid before conversion and grid information after conversion that corresponds a grid after conversion is stored in the storage unit 27. It is assumed that Sσ in the table is experimentally calculated in advance such that scattering characteristics by the grid before conversion can be relatively converted into scattering characteristics by the grid after conversion. Then, the scattered radiation removal unit 23 acquires first grid information corresponding to the grid (or a virtual grid) that is actually used as the grid information before conversion, acquires second grid information corresponding to a desired virtual grid as the grid information after conversion, and acquires Sσ corresponding to the first grid information and the second grid information on the basis of the table. Then, scattered radiation removal unit 23 calculates the primary radiation component Icp(x, y) and the scattered radiation component Ics(x, y) on the basis of the acquired Sσ and Expressions (1) and (2) in which Io(x, y) is, for example, 1. Then, the scattered radiation removal unit 23 may calculate the conversion function, that is, the scattered radiation content distribution S(x, y), on the basis of the calculated primary radiation component Icp(x, y) and scattered radiation component Ics(x, y), using Expression (3).

In addition, the scattered radiation removal unit 23 may acquire the first grid characteristic (primary radiation transmittance Tp1 and scattered radiation transmittance Ts1) corresponding to the grid (or a virtual grid) that is actually used and the second virtual grid characteristic (primary radiation transmittance Tp2 and scattered radiation transmittance Ts2) corresponding to a desired virtual grid, for the scattered radiation transmittance Ts and the primary radiation transmittance Tp. Then, in order to relatively convert scattering characteristics by the first grid before conversion into scattering characteristics by the second grid after conversion, the scattered radiation removal unit 23 may acquire Tp2/Tp1 as the primary radiation transmittance Tp and acquire Ts2/Ts1 as the scattered radiation transmittance Ts. Then, the scattered radiation removal unit 23 may apply the acquired scattered radiation transmittance Ts (=Ts2/Ts1) and primary radiation transmittance Tp (=Tp2/Tp1) to Expression (22) to calculate the conversion function Q and may perform the scattered radiation removal process, using the conversion function Q, similarly to the third embodiment. In the above-mentioned Expression (22), in some cases, the conversion function Q(x, y) is greater than 1 in a case in which the scattered radiation transmittance Ts2 of the second grid characteristic is greater than the scattered radiation transmittance Ts1 of the first grid characteristic.

The first grid characteristic and the second grid characteristic may be acquired by any method. For example, a table in which the grid characteristics (the primary radiation transmittance Tp and the scattered radiation transmittance Ts) that are calculated in advance by, for example, experiments are associated with each grid information item is prepared and stored in the storage unit 27. Then, the scattered radiation removal unit 23 may acquire the first and second grid information items and acquire the first and second grid characteristics corresponding to the first and second grid information items on the basis of the table. In addition, the first and second grid characteristics that are input by the user through the input unit 8 may be acquired. Grid information that is input from the input unit 8 may be acquired. For example, as described in JP2003-260053A, protrusions corresponding to the type of grid may be formed on a grid and the protrusion may be detected to acquire grid information.

In the first to third embodiments, both the processed radiographic image and the radiographic image before processing may be displayed such that one of the radiographic images to be used for diagnosis can be selected.

There is a case in which time-dependent comparison and observation is performed, using the previous radiographic images, in order to diagnose the healing state or progress state of a disease. In a case in which a radiographic image (a radiographic image with a grid) which is captured without using a scattered radiation removal grid is compared with a radiographic image (referred to as a radiographic image without a grid) which is captured using the scattered radiation removal grid, it is preferable to correct the conditions of the scattered radiation removal process according to this embodiment, on the basis of the processing conditions when a process of removing a stripe pattern caused by the grid is performed for the radiographic image with a grid such that the radiographic image with a grid and the radiographic image without a grid have the same image quality.

In the above-described embodiments, the scattered radiation removal process is performed, using the radiographic image acquired by the imaging device 1 which captures the radiographic image of the subject using the radiation detector 5. However, the invention can be applied to the structures disclosed in JP1996-266529A (JP-H08-266529A) and JP1997-24039A (JP-H09-24039A) in which the radiographic image information of the subject is stored and recorded on a storage phosphor sheet as a radiation detector and the radiographic image is photoelectrically read and acquired from the storage phosphor sheet and is then used.

What is claimed is:
1. A radiographic image processing device comprising:
at least one hardware processor configured to implement:
a frequency decomposition unit for performing frequency decomposition for a first radiographic image which is captured by irradiating a subject with radiation and acquiring a plurality of band images indicating a plurality of frequency components of the first radiographic image;
a scattered radiation removal unit for calculating a scattered radiation component that is caused by the subject and is included in a second radiographic image of the subject which has a linear relationship with an amount of radiation, using the second radiographic image, and removing the scattered radiation component from the second radiographic image to acquire a scattered-radiation-removed radiographic image;
a conversion function determination unit for determining a conversion function for converting at least one of the band images according to the scattered radiation component included in the second radiographic image;
a conversion unit for converting the at least one band image, using the conversion function, and generating a converted band image; and
a reconstruction unit for reconstructing the scattered-radiation-removed radiographic image and the converted band image to acquire a processed radiographic image,
wherein the first radiographic image has a pixel value that has a linear relationship with a logarithmic amount of radiation, and
wherein the second radiographic image is obtained by performing inverse logarithmic conversion for the first radiographic image.

2. The radiographic image processing device according to claim 1,
wherein the conversion function determination unit determines the conversion function on the basis of a ratio of the scattered radiation component to a sum of a primary radiation component included in the radiation and the scattered radiation component.

3. The radiographic image processing device according to claim 2,
wherein the scattered radiation removal unit calculates the scattered radiation component and the primary radiation component, using a body thickness distribution of the subject, and
the conversion function determination unit calculates the ratio from the calculated scattered radiation component and the calculated primary radiation component.

4. The radiographic image processing device according to claim 3, wherein the at least one hardware processor is further configured to implement:
a body thickness estimation unit for estimating the body thickness distribution on the basis of the second radiographic image.

5. The radiographic image processing device according to claim 1,
wherein the reconstruction unit performs logarithmic conversion for the scattered-radiation-removed radiographic image and reconstructs the logarithmically-converted scattered-radiation-removed radiographic image and the converted band image to acquire the processed radiographic image.

6. The radiographic image processing device according to claim 1, wherein the at least one hardware processor is further configured to implement:
a characteristic acquisition unit for acquiring virtual grid characteristics which are characteristics of a virtual grid that is assumed to be used in order to remove scattered radiation when an image of the subject is captured, wherein the scattered radiation removal unit calculates the scattered radiation component on the basis of the virtual grid characteristics, and the conversion function determination unit determines the conversion function on the basis of the calculated scattered radiation component.

7. The radiographic image processing device according to claim 1, wherein, when a pixel value of the band image is greater than a predetermined threshold value, the conversion function determination unit determines the conversion function to be a non-linear function that suppresses the pixel value.

8. A radiographic image processing method comprising:

performing frequency decomposition for a first radiographic image which is captured by irradiating a subject with radiation and acquiring a plurality of band images indicating a plurality of frequency components of the first radiographic image;

calculating a scattered radiation component that is caused by the subject and is included in a second radiographic image of the subject which has a linear relationship with an amount of radiation, using the second radiographic image;

removing the scattered radiation component from the second radiographic image to acquire a scattered-radiation-removed radiographic image;

determining a conversion function for converting at least one of the band images according to the scattered radiation component included in the second radiographic image;

converting the at least one band image, using the conversion function, and generating a converted band image; and reconstructing the scattered-radiation-removed radiographic image and the converted band image to acquire a processed radiographic image, wherein the first radiographic image has a pixel value that has a linear relationship with a logarithmic amount of radiation, and wherein the second radiographic image is obtained by performing inverse logarithmic conversion for the first radiographic image.

9. A non-transitory recording medium having stored therein a radiographic image processing program that causes a computer to perform:

a step of performing frequency decomposition for a first radiographic image which is captured by irradiating a subject with radiation and acquiring a plurality of band images indicating a plurality of frequency components of the first radiographic image;

a step of calculating a scattered radiation component that is caused by the subject and is included in a second radiographic image of the subject which has a linear relationship with an amount of radiation, using the second radiographic image;

a step of removing the scattered radiation component from the second radiographic image to acquire a scattered-radiation-removed radiographic image;

a step of determining a conversion function for converting at least one of the band images according to the scattered radiation component included in the second radiographic image;

a step of converting the at least one band image, using the conversion function, and generating a converted band image; and a step of reconstructing the scattered-radiation-removed radiographic image and the converted band image to acquire a processed radiographic image, wherein the first radiographic image has a pixel value that has a linear relationship with a logarithmic amount of radiation, and wherein the second radiographic image is obtained by performing inverse logarithmic conversion for the first radiographic image.

10. The radiographic image processing device according to claim 1, wherein the conversion function determination unit determines the conversion function based on the second radiographic image before the scattered radiation component is subtracted and the second radiographic image after the scattered radiation component is subtracted.

* * * * *